(12) United States Patent
Serban et al.

(10) Patent No.: US 12,187,673 B2
(45) Date of Patent: Jan. 7, 2025

(54) APPARATUS FOR THE HYDROGENATION OF OLEFINS

(71) Applicant: UOP LLC, Des Plaines, IL (US)

(72) Inventors: Manuela Serban, Northbrook, IL (US); Chunqing Liu, Arlington Heights, IL (US); Ashish Mathur, Gurgaon (IN); Saikrishna Laxmirajam Gosangari, Gurugram (IN); Charles Luebke, Mount Prospect, IL (US); Eseoghene Jeroro, Chicago, IL (US); Chad R. Huovie, Park Ridge, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 18/599,190

(22) Filed: Mar. 7, 2024

(65) Prior Publication Data

US 2024/0246888 A1    Jul. 25, 2024

Related U.S. Application Data

(63) Continuation of application No. 18/059,807, filed on Nov. 29, 2022, now Pat. No. 11,939,283.

(60) Provisional application No. 63/411,693, filed on Sep. 30, 2022.

(51) Int. Cl.
*C07C 5/03* (2006.01)
*C01B 3/06* (2006.01)
*C07C 1/24* (2006.01)
*C25B 1/04* (2021.01)

(52) U.S. Cl.
CPC .................. *C07C 5/03* (2013.01); *C07C 1/24* (2013.01); *C01B 3/06* (2013.01); *C07C 2521/04* (2013.01); *C25B 1/04* (2013.01)

(58) Field of Classification Search
CPC ......... C07C 5/03; C07C 1/24; C07C 2521/04; C07C 2/12; C01B 3/06; C25B 1/04; C10G 69/126
See application file for complete search history.

(56) References Cited

U.S. PATENT DOCUMENTS

2004/0192982 A1*  9/2004  Kuechler ............... C10G 45/40
                                                              585/259

* cited by examiner

*Primary Examiner* — Ali Z Fadhel
(74) *Attorney, Agent, or Firm* — Paschall & Associates, LLC; James C. Paschall

(57) ABSTRACT

An integrated apparatus for hydrogenating olefins wherein the hydrogen stream is generated from the electrolysis of water is described. Water is derived from a first reaction step wherein a first feed stream comprising oxygenated hydrocarbons is reacted to produce a first reacted product stream comprising olefins and a second reacted product stream comprising water. The second reacted product stream is electrolyzed to produce an electrolyzer product stream comprising hydrogen. Hydrogen is used to hydrogenate olefins. A paraffin stream can be obtained from the hydrogenated effluent.

10 Claims, 1 Drawing Sheet

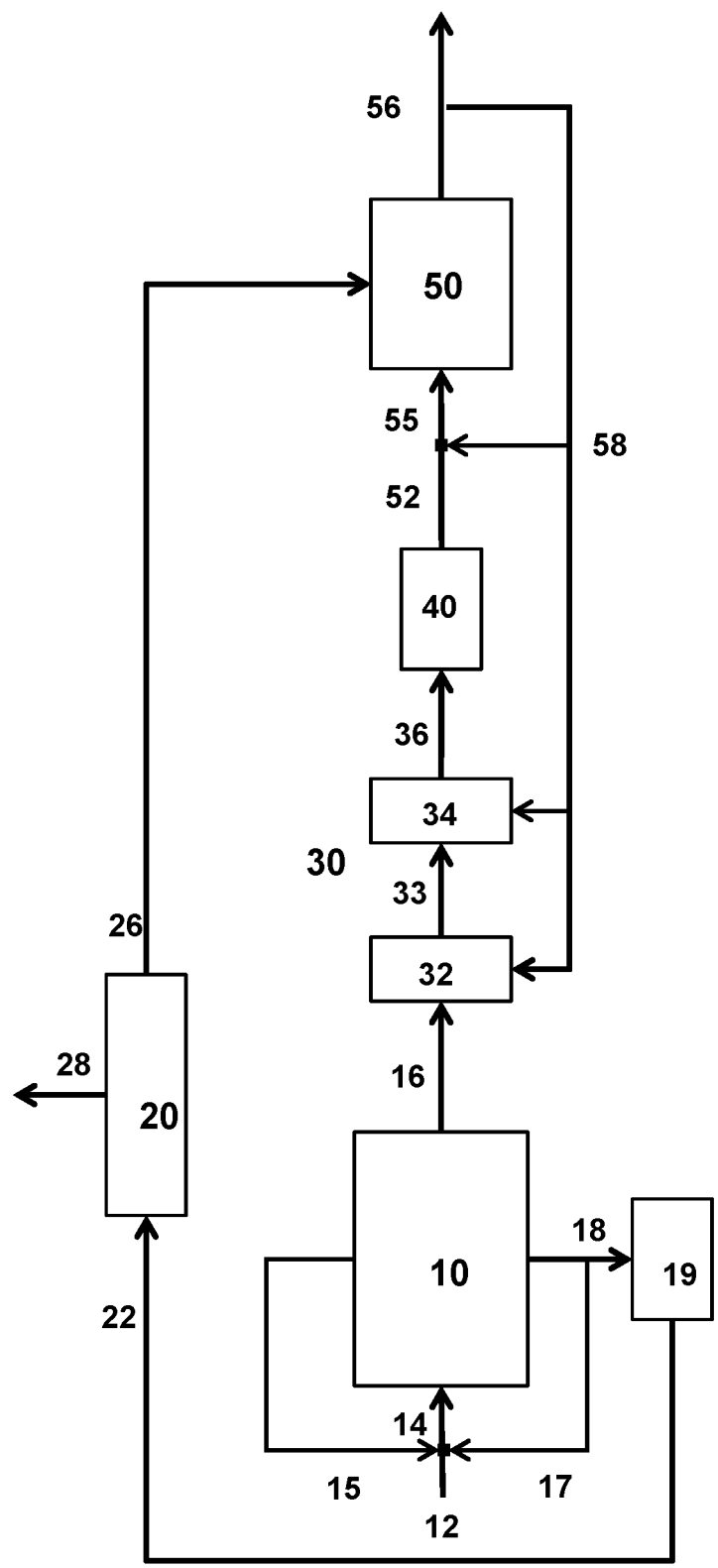

APPARATUS FOR THE HYDROGENATION OF OLEFINS

FIELD

The field is the hydrogenation of olefin containing streams with a hydrogen stream generated by electrolysis of water.

BACKGROUND

Jet fuel is one of the few petroleum fuels that cannot be replaced easily by electrical motor systems because a high energy output is required to power planes. Jet fuel is comprised of about 75% paraffins and about 25% aromatics as described in ASTM D1655. Synthesized hydrocarbons from sources including alcohol-to-jet (ATJ-SPK) and hydrothermal conversion of fatty acid esters (CHJ) may also be used as jet fuels as described in ASTM D7566. These sources may have aromatic contents as low as 0.5 wt %. Large incentives are currently available for green jet fuel in certain regions.

Ethanol is a bio-derived alcohol that can be dehydrated to ethylene. Ethylene can be dimerized into olefins such as C4, C6 and C8 olefins. Olefin oligomerization is a process that can oligomerize smaller olefins into larger olefins. More specifically, it can convert olefins including dimerized olefins into a distillate including jet fuel and diesel range products. The oligomerized distillate can be saturated for use as transportation fuels with high stability.

Processes utilizing electrochemical cells for chemical conversions have also been described. Generally, an electrochemical cell contains an anode, a cathode, and an electrolyte. Catalysts can be placed on the anode, the cathode, and/or in the electrolyte to promote the desired chemical reactions. During operation, reactants or a solution containing reactants are fed into the cell. A voltage (potential difference) is then applied between the anode and the cathode, to promote the desired electrochemical reaction. When water is the reactant, and products comprising oxygen and hydrogen are produced, the reaction is often called water splitting or electrolysis, and the reactor an electrolyzer.

Thus, there is a need for processes for hydrogenation of olefins to allow utilization of bio-derived feedstocks such as ethanol to be used as the source of transportation fuels.

BRIEF SUMMARY

We have formulated an integrated apparatus for hydrogenating olefins wherein the hydrogen stream is generated from electrolysis of water. The water is derived from a first reaction step wherein a first feed stream is reacted to produce a first reacted product stream comprising olefins and a second reacted product stream comprising water and the second reacted product stream is electrolyzed to produce an electrolyzer product stream comprising hydrogen. A paraffin stream can be obtained from the hydrogenated effluent.

BRIEF DESCRIPTION OF THE DRAWING

The FIGURE is a schematic elevational drawing of an apparatus of the present disclosure.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

As used herein, the term "predominant", "predominate", or "predominantly" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

The term "unit" is to be understood to refer to one or more process steps comprising a chemical transformation. At the heart of a unit is one or more catalytic reactors or separation vessels necessary to accomplish the transformation. A unit may further comprise additional separation vessels including fractionation column(s) to separate product streams. A unit may further comprise pretreatment steps for the chemical transformation. Taken together, "unit" comprises one or more reactors or separation vessels and separation steps and pretreatment steps, whether or not shown in the diagram or explicitly discussed in the specification.

As used herein, the term "T5", "T90" or "T95" means the temperature at which 5 mass percent, 90 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, the term "diesel" and/or "distillate" means hydrocarbons boiling in the range of an IBP between about 125° C. (257° F.) and about 175° C. (347° F.) or a T5 between about 150° C. (302° F.) and about 200° C. (392° F.) and the "diesel cut point" comprising a T95 between about 343° C. (650° F.) and about 399° C. (750° F.) using the TBP distillation method or a T90 between 280° C. (536° F.) and about 340° C. (644° F.) using ASTM D-86. The term "green ° ° ° ° diesel" or "green distillate" means diesel comprising hydrocarbons not sourced from fossil fuels.

As used herein, the term "jet fuel" means hydrocarbons boiling in the range of a T10 between about 190° C. (374° F.) and about 215° C. (419° F.) and an end point of between about 290° C. (554° F.) and about 310° C. (590° F.). The term "green jet fuel" means jet fuel comprising hydrocarbons not sourced from fossil fuels.

As used herein, "electrolyzer" is meant to indicate a device containing a cathode (negative charge), an anode (positive charge) and a membrane. The entire system may also contain pumps, vents, storage tanks, a power supply, separator and/or other components. Typically, these devices are used to cause an electrochemical reaction such as water electrolysis within the cell stacks of the electrolyzer unit. Electricity is applied to the anode and cathode across the membrane which for the case of water electrolysis causes the water to split into its component molecules, hydrogen ($H_2$) and oxygen ($O_2$).

The term "cathode" means an electrode through which the conventional current exits from a polarized electrical device and electrons flow in from an outside or external circuit connected to the cell. Reduction reactions occur at the cathode.

The term "anode" means an electrode through which the conventional current enters into a polarized electrical device and electrons flow out into an outside or external circuit connected to the cell. Oxidation reactions occur at the anode.

DETAILED DESCRIPTION

The apparatus disclosed comprises providing a first feed stream comprising oxygenated hydrocarbons to a first reaction unit, reacting said first feed stream to produce a first reacted product stream comprising olefins and a second reacted product stream comprising water, electrolyzing said second reacted product stream to produce an electrolyzer product stream comprising hydrogen, providing a first hydrogenation feed stream comprising hydrogen and a second hydrogenation feed stream comprising olefins to a hydrogenation unit, and hydrogenating said second hydrogenation feed stream over a hydrogenation catalyst at hydrogenation reaction conditions to form a hydrogenation product stream comprising paraffins.

Turning to the drawing of FIG. 1, the first feed stream in line 12 to the first reaction unit 10 may comprise oxygenated hydrocarbons. Oxygenated hydrocarbons include ethanol, propanol, other alcohols, and/or triglycerides. Preferably, the oxygenated hydrocarbons have a biological source such as fermentation or from a plant oil. In an exemplary embodiment, the first feed stream in line 12 may comprise ethanol. The first feed stream in line 12 may predominantly comprise ethanol. The first reaction unit 10 may comprise ethanol dehydration.

Dehydration converts ethanol to ethylene and water. Ethanol dehydration is a highly endothermic reaction. Steam may be added to the reactor(s) to help control endothermicity and reduce coke laydown to improve the stability of the catalyst. A water recycle stream in line 17 may additionally comprise a portion of the combined first feed stream in line 14. Unconverted ethanol may also be recycled in a recycle feed stream in line 15 to comprise a portion of the combined first feed stream in line 14.

The combined first feed stream may be heated in one or more stages through heat exchangers, fired heaters, or combinations thereof. In an exemplary embodiment, a portion of the heat generated in hydrogenation unit 50 is captured as hot steam and used to help heat the first combined feed stream in line 14 up to a temperature around 400° C. Thus, the hydrogenation unit 50 and the first reaction unit 10 may be heat integrated. Greater than 10% or greater than 25% or greater than 50% of the necessary heat for reaction in the first reaction unit 10 may be supplied via heat integration from hydrogenation unit 50. A fired heater may also help provide sufficient heat. The first combined feed stream may be further heated to a dehydration reaction temperature of from about 400° C. to about 550° C. before passing over a dehydration catalyst at a pressure of from about 317 kPa (gauge) (45 psig) to about 2068 kPa (300 psig) or from about 345 kPa (50 psig) to about 630 kPa (gauge) (90 psig). An acceptable pressure may also be from about 1379 kPa (200 psig) to about 1724 kPa (250 psig).

In an aspect, the ethanol dehydration catalyst may be an alumina-based catalyst. The dehydration catalyst may substantially comprise gamma alumina.

In an alternate embodiment, the first reaction unit 10 may comprise hydrotreating. Suitable feed streams in line 12 to the hydrotreatment unit may comprise triglycerides derived from plant oils. Renewable feedstocks that can be used in the present invention include any of those which comprise glycerides and free fatty acids (FFA). Examples of these feedstocks include, but are not limited to, canola oil, corn oil, soy oils, rapeseed oil, soybean oil, colza oil, tall oil, sunflower oil, hempseed oil, olive oil, linseed oil, coconut oil, castor oil, peanut oil, palm oil, mustard oil, cottonseed oil, tallow, yellow and brown greases, lard, train oil, fats in milk, fish oil, algal oil, sewage sludge, cuphea oil, camelina oil, jatropha oil, curcas oil, babassu oil, palm kernel oil, crambe oil, and the like. Biorenewable is another term used to describe these feedstocks. The glycerides, FFAs, and fatty acid alkyl esters, of the typical vegetable oil or animal fat contain aliphatic hydrocarbon chains in their structure which have about 8 to about 24 carbon atoms with a majority of the oils containing high concentrations of fatty acids with 16 and 18 carbon atoms. Mixtures or co-feeds of renewable feedstocks and fossil fuel derived hydrocarbons may also be used as the feedstock. Other feedstock components which may be used, especially as a co-feed component in combination with the above listed feedstocks, include spent motor oil and industrial lubricants, used paraffin waxes, liquids derived from gasification of coal, biomass, or natural gas followed by a downstream liquefaction step such as Fischer-Tropsch technology; liquids derived from depolymerization, thermal or chemical, of waste plastics such as polypropylene, high density polyethylene, and low density polyethylene; and other synthetic oils generated as byproducts from petrochemical and chemical processes. Mixtures of the above feedstocks may also be used as co-feed components. One advantage of using a co-feed component is the transformation of what has been considered to be a waste product from a fossil fuel based or other process into a valuable co-feed component to the current process. In this alternate embodiment, the first feed stream in line 12 may be contacted with a multifunctional catalyst or a set of catalysts having hydrogenation, deoxygenation, isomerization, and selective hydrocracking functions to produce a reaction effluent comprising water, carbon oxides, light hydrocarbon gasses, hydrogen and paraffinic hydrocarbons. The water, carbon oxides, light hydrocarbon gasses, and hydrogen are separated from the reaction effluent to generate a liquid stream comprising the paraffinic hydrocarbons.

As mentioned above, the multifunctional catalyst or set of catalysts comprise deoxygenation, hydrogenation, isomerization and selective hydrocracking functions. The deoxygenation and hydrogenation functions, which may be the same or separate active sites, may be noble metals such as a platinum group metals including but not limited to ruthenium, rhodium, palladium, platinum, and mixtures thereof at levels ranging from about 0.05 to about 2.0 weight-% of the catalytic composite. Some catalysts may contain up to about 10 wt.-% platinum or palladium on carbon. Examples of other active sites that may be employed to provide the deoxygenation and hydrogenation functions are sulfided base metals such as sulfided NiMo or sulfided NiW. A base metal is a metal which oxidizes when heated in air, and other base metals, in addition to nickel, molybdenum and tungsten, which may be a catalyst component herein include iron, lead, zinc, copper, tin, germanium, chromium, titanium, cobalt, rhenium, indium, gallium, uranium, dysprosium, thallium and mixtures and compounds thereof. As to the isomerization and selective hydrocracking functions, the second portion of the catalyst composite may contain a zeolite with an acid function capable of catalyzing the isomerization and selective hydrocracking reactions. The zeolite concentration can range from about 1 to about 99 weight percent of the catalyst composite depending upon the type of zeolite employed and the operating conditions. In one embodiment, the zeolite contains medium to large size pores with 10-12 member rings such as BEA, MOR, MFI, or FAU. In other embodiments, the cracking function is a non-crystalline acid site found in materials such as amorphous silica-alumina. In another embodiment, a portion of the support has high external surface area, greater than about 150 m.sup.2/g, or large mesopores, greater than 45 Angstrom average pore diameter, for maximum accessibility of the large triglyceride molecules to the catalytic active sites. This is beneficial since a highly porous structure with large openings will reduce diffusion problems that might otherwise prevent the large glyceride molecules from contacting the active sites of the catalyst. Furthermore, large pores will prevent diffusional resistance for the aviation-range paraffins produced in this catalytic process and present further cracking to lower value light products. Examples of catalysts, or sets of catalysts, successful in catalyzing the deoxygenation, hydrogenation, isomerization, and selective hydrocracking reactions in the same reaction zone include platinum dispersed on a support containing Y-zeolite. Another example is platinum and palladium on a support containing Y-zeolite bound with amorphous silica alumina. An example of a set of catalysts include sulfided NiMo supported on amorphous silica alumina and platinum supported on amorphous silica alumina.

The inlet temperature of the catalyst bed within first reaction unit 10 in this embodiment may be in the range of from about 150° C. to about 454° C. (about 300° F. to about 850° F.), and the inlet pressure should be above about 1379 kPa gauge to about 13,790 kPa gauge (200 to about 2,000 psig). The feed stream is admixed with sufficient hydrogen to provide hydrogen circulation rate of about 168 to 1684 nl/l (1000 to 10000 Standard Cubic Feet/Barrel, hereafter SCFB) and passed into the reactor containing the catalyst or set of catalysts. The hydrogen may be primarily derived from a recycle gas stream which may pass through purification facilities for the removal of acid gases. Fresh hydrogen may also be delivered from the first electrolyzed product stream. The hydrogen rich gas admixed with the feed and in one embodiment any recycle stream comprising hydrocarbons will contain at least 90 mol percent hydrogen. The feed rate in terms of liquid hourly space velocity (L.H.S.V.) will normally be is within the broad range of about 0.3 to about 5 hr$^{-1}$, with a L.H.S.V. below 1.2 being used in one embodiment.

The first reaction unit 10 may produce a plurality of product streams after reaction of the first feed stream. These may include a recycle feed steam in line 15, first reacted product stream in line 16, and a second reacted product stream in line 18. Additional streams may be produced. Light gas streams and/or heavy olefin streams may be produced. The first reacted product stream in line 16 may comprise olefins. The second reacted product stream in line 18 may comprise water and preferably predominantly comprises water. The second reacted product stream in line 18 may be passed to a surge tank 19 for accumulation of sufficient product or to be treated and/or purified prior to further processing.

If the first reaction unit comprises ethanol dehydration, the first reacted product stream in line 16 may comprise ethylene or may predominantly comprise ethylene. The first reacted product stream in line 16 may exit the first reaction unit 10 at a pressure of from about 317 kPa (gauge) (45 psig) to about 630 kPa (gauge) (90 psig) or from about 345 kPa (gauge) (50 psig) to about 414 kPa (gauge) (60 psig). The first reacted product stream may be compressed using one or more stages of compression prior to further reaction in second reaction unit 30. A first stage compressor may compress the first reacted product stream to a first pressure of about 350 kPa (gauge) (50 psig) to about 1225 kPa (gauge) (175 psig). A second stage compressor may compress the first reacted product stream to a second pressure of about 455 kPa (gauge) (165 psig) to about 3220 kPa (gauge) (460 psig). A third stage compress may compress the first reacted product stream to a third pressure of from about 5.6 MPag (800 psig) to about 8.4 MPag (1200 psig).

In an aspect, the second reacted product stream comprising water may be generated after one or more compression stages. Preferably, the second reacted product stream is in the liquid phase. The second reacted product stream in line 18 may be fed to an electrolyzer unit 20 via electrolyzer feed line 22 either directly or after passing through the surge tank 19. The electrolyzer unit comprises an electrolyzer.

The electrolyzer unit 20 may comprise an electrolyzer catalyst. The electrolyzer catalyst may comprise platinum (Pt). The electrolyzer catalyst may comprise platinum loaded on carbon. Loadings of platinum on carbon may range from about 0.1 mg$^2$/cm to about 1 mg$^2$/cm. The electrolyzer feed stream comprising water from the second reacted product stream may be further augmented to comprise an aqueous alkaline solution. Potassium hydroxide (KOH) may be a preferred component of the electrolyzer feed stream due to high conductivity. Other electrolytes such as the bicarbonate, sulfate or chloride (KHCO$_3$, K$_2$SO$_4$, and KCl) may also be used. No electrolyte may be used. The concentration of KOH in the electrolyzer feed stream may range from about 0.1 M to about 1.5 M. Current density in the electrolyzer unit 20 may be related to the concentration of KOH in the electrolyzer anode reactant, with higher current densities achieved at higher concentration of KOH.

The concentration of KOH in the electrolyzer feed stream may range from about 0.1 M to about 1.5 M. A voltage of from about 1.5V to about 5V may be applied between the anode and the cathode within the electrolyzer unit 20. Lower applied voltages are preferable. A voltage of less than about 2V may be applied between the electrolyzer anode and electrolyzer cathode.

The electrolyzer 20 converts water into hydrogen and oxygen. The first electrolyzed product stream in line 26 may comprise hydrogen and preferably predominantly comprises hydrogen. The first electrolyzed product stream may comprise greater than 95% hydrogen, or greater than 98% hydrogen, or greater than 99% hydrogen. The first electrolyzed product stream may comprise nearly 100% hydrogen, such as 99.9% hydrogen. In an aspect, the first electrolyzed product stream in line 26 is at a temperature of from about 40° C. (104° F.) to about 120° C. (248° F.) and a pressure of from about 35 barg (508 psig) to about 70 barg (1015 psig). The second electrolyzed product stream in line 28 may comprise oxygen. The second electrolyzed product stream may predominantly comprise oxygen. Oxygen may be a valuable product and recovered for use as feed to a fuel cell for power generation or medical purpose or other industrial applications.

The process may further comprise reacting said first reacted product stream in line 16 in a second reaction unit 30 to produce a third reacted product stream in line 36 comprising olefins with a higher average molecular weight than the first reacted product stream in line 16. An exemplary process in second reaction unit 30 comprises one or more oligomerization steps over one or more oligomerization catalysts in an oligomerization unit at oligomerization conditions to provide the third reacted product stream in line 36 comprising olefins.

Oligomerization may comprise dimerizing an olefin stream comprising ethylene followed by further oligomerizing the ethylene dimers and ethylene oligomers. The resulting oligomers can be separated to provide a distillate stream which may be saturated to provide distillate fuels. A saturated stream may be recycled to ethylene dimerization as diluent to absorb the dimerization and/or oligomerization exotherm. Additionally, the olefin stream in line 16 may be split and charged to more than one catalyst beds also to manage the exotherm. The dimerization product of a catalyst bed which may contain unconverted olefins, also passes to a downstream bed hence boosting overall per pass conversion. Additionally, dimerization products of upstream catalyst beds serve as additional diluent to absorb the exotherm in a downstream catalyst bed.

The second reaction unit feed stream in line 16 may comprise substantial ethylene. The feed stream may predominantly comprise ethylene. In an aspect, the feed stream may comprise at least 95 mol % ethylene.

The second reaction unit feed stream in line 16 may be at a temperature of about 60° C. (140° F.) to about 190° C. (374° F.), preferably about 100° C. (212° F.) to about 170° C. (338° F.) and a pressure of about 5.6 MPag (800 psig) to about 8.4 MPag (1200 psig).

The second reaction unit 30 may comprise a dimerization reactor 32 and an oligomerization reactor 34. The dimerization and oligomerization reactors may be one reactor or may be multiple reactors. The second reaction unit feed stream may be initially contacted with a dimerization catalyst to dimerize the ethylene to dimers and then contacted with an oligomerization catalyst to oligomerize dimerized ethylene. The oligomerization catalyst may be placed upstream of the dimerization catalyst.

The dimerization reaction may take place predominantly in the liquid phase or in a mixed liquid and gas phase at a LHSV 0.5 to 10 $hr^{-1}$ on an olefin basis. We have found that a predominant fraction of ethylene in the olefin stream converts to higher olefins. Typically, at least 90 to about 95 mol % of ethylene will dimerize across a dimerization catalyst bed. The ethylene will initially dimerize over the catalyst to butenes.

The dimerization catalyst may comprise a metal supported catalyst. The dimerization catalyst is preferably an amorphous silica-alumina base with a metal from either Group VIII and/or Group VIB in the periodic table using Chemical Abstracts Service notations. In an aspect, the catalyst has a Group VIII metal promoted with a Group VIB metal. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Catalysts for the present invention may have a Low Temperature Acidity Ratio of at least about 0.15, suitably of about 0.2, and preferably greater than about 0.25, as determined by Ammonia Temperature Programmed Desorption (Ammonia TPD) as described hereinafter. Additionally, a suitable catalyst will have a surface area of between about 50 and about 400 $m^2/g$ as determined by nitrogen BET.

A preferred dimerization catalyst is described as follows. The preferred dimerization catalyst comprises an amorphous silica-alumina support. One of the components of the catalyst support utilized in the present invention is alumina. The alumina may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A particularly preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina. Another component of the catalyst support is an amorphous silica-alumina. A suitable silica-alumina with a silica-to-alumina ratio of 2.6 is available from CCIC, a subsidiary of JGC, Japan.

Another component utilized in the preparation of the catalyst utilized in the present invention is a surfactant. The surfactant is preferably admixed with the hereinabove described alumina and the silica-alumina powders. The resulting admixture of surfactant, alumina and silica-alumina is then formed, dried and calcined as hereinafter described. The calcination effectively removes by combustion the organic components of the surfactant but only after the surfactant has dutifully performed its function in accordance with the present invention. Any suitable surfactant may be utilized in accordance with the present invention. A preferred surfactant is a surfactant selected from a series of commercial surfactants sold under the trademark "Antarox" by Solvay S.A. The "Antarox" surfactants are generally characterized as modified linear aliphatic polyethers and are low-foaming biodegradable detergents and wetting agents.

A suitable silica-alumina mixture is prepared by mixing proportionate volumes silica-alumina and alumina to achieve the desired silica-to-alumina ratio. In an embodiment, about 75 to about 95 wt-% amorphous silica-alumina with a silica-to-alumina ratio of 2.6 and about 10 to about 20 wt-% alumina powder will provide a suitable support. In an embodiment, other ratios of amorphous silica-alumina to alumina may be suitable.

Any convenient method may be used to incorporate a surfactant with the silica-alumina and alumina mixture. The surfactant is preferably admixed during the admixture and formation of the alumina and silica-alumina. A preferred method is to admix an aqueous solution of the surfactant with the blend of alumina and silica-alumina before the final formation of the support. It is preferred that the surfactant be present in the paste or dough in an amount from about 0.01 to about 10 wt-% based on the weight of the alumina and silica-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough mixture of alumina, silica-alumina, surfactant and water through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 µm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

Typical characteristics of the amorphous silica-alumina supports utilized herein are a total pore volume, average pore diameter and surface area large enough to provide substantial space and area to deposit the active metal components. The total pore volume of the support, as measured by conventional mercury porosimeter methods, is usually about 0.2 to about 2.0 cc/gram, preferably about 0.25 to about 1.0 cc/gram and most preferably about 0.3 to about 0.9 cc/gram. Ordinarily, the amount of pore volume of the support in pores of diameter greater than 100 angstroms is less than about 0.1 cc/gram, preferably less than 0.08 cc/gram, and most preferably less than about 0.05 cc/gram. Surface area, as measured by the B.E.T. method, is typically above 50 m$^2$/gram, e.g., above about 200 m$^2$/gram, preferably at least 250 m$^2$/gram, and most preferably about 300 m$^2$/gram to about 400 m$^2$/gram.

To prepare the catalyst, the support material is compounded, as by a single impregnation or multiple impregnations of a calcined amorphous refractory oxide support particles, with one or more precursors of at least one metal component from Group VIII or VIB of the periodic table. The Group VIII metal, preferably nickel, should be present in a concentration of about 0.5 to about 15 wt-% and the Group VIB metal, preferably tungsten, should be present in a concentration of about 0 to about 12 wt-%. The impregnation may be accomplished by any method known in the art, as for example, by spray impregnation wherein a solution containing the metal precursors in dissolved form is sprayed onto the support particles. Another method is the multi-dip procedure wherein the support material is repeatedly contacted with the impregnating solution with or without intermittent drying. Yet other methods involve soaking the support in a large volume of the impregnation solution or circulating the support therein, and yet one more method is the pore volume or pore saturation technique wherein support particles are introduced into an impregnation solution of volume just sufficient to fill the pores of the support. On occasion, the pore saturation technique may be modified, so as to utilize an impregnation solution having a volume between 10 percent less and 10 percent more than that which will just fill the pores.

If the active metal precursors are incorporated by impregnation, a subsequent or second calcination at elevated temperatures, as for example, between 399° C. (750° F.) and 760° C. (1400° F.), converts the metals to their respective oxide forms. In some cases, calcinations may follow each impregnation of individual active metals. A subsequent calcination yields a catalyst containing the active metals in their respective oxide forms.

A preferred dimerization catalyst of the present invention has an amorphous silica-alumina base impregnated with 0.5-15 wt-% nickel in the form of 3.175 mm (0.125 inch) extrudates and a density of about 0.45 to about 0.65 g/ml. It is also contemplated that metals can be incorporated onto the support by other methods such as ion-exchange and co-mulling.

The dimerization catalyst can be regenerated upon deactivation. Suitable regeneration conditions include subjecting the catalyst, for example, in situ, to hot air at 500° C. for 3 hours. To facilitate regeneration without downtime, a swing bed arrangement may be employed with an alternative dimerization reactor. The regeneration gas may comprise air with an increased or decreased concentration of oxygen. Activity and selectivity of the regenerated catalyst is comparable to fresh catalyst.

To manage the exotherm, the feed stream in line 16 may be diluted with a diluent stream to provide a diluted olefin stream to help absorb the exotherm. The diluent stream may comprise a paraffin stream in a diluent line 58. The first diluted olefin stream may comprise no more than 25 wt % olefins, suitably no more than 10 wt % olefins and preferably no more than 6 wt % olefins. The first diluted olefin stream may comprise no more than 25 wt % ethylene, suitably no more than 10 wt % ethylene and preferably no more than 6 wt % ethylene. A dimerized stream may be produced in line 33.

The second reaction unit 30 may further comprise an oligomerization reactor 34. The oligomerization reactor 34 may be in downstream communication with the dimerization reactor 32 via line 33. Alternately, the oligomerization reactor 34 may be in upstream communication with the dimerization reactor 32. The oligomerization reactor 34 preferably operates in a down flow operation. However, upflow operation may be suitable. The charge oligomerization stream is contacted with the oligomerization catalyst causing the C2-C8 olefins to dimerize and trimerize to provide distillate range olefins. A predominance of the butenes in the charge oligomerization stream is oligomerized. In an embodiment, at least 99 mol % of butenes in the charge oligomerization stream are oligomerized. A third reacted product stream in line 36 with an increased average carbon number greater than the second reaction unit feed stream in line 16 exits the oligomerization reactor 34 and second reaction unit 30 in line 36.

The oligomerization catalyst may comprise a zeolitic catalyst. The zeolite may comprise between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. 3-letter codes indicating a zeotype are as defined by the Structure Commission of the International Zeolite Association and are maintained at http://www.iza-structure.org/databases. UZM-8 is as described in U.S. Pat. No. 6,756,030. In a preferred aspect, the oligomerization catalyst may comprise a zeolite with a framework having a ten-ring pore structure. Examples of suitable zeolites having a ten-ring pore structure include TON, MTT, MFI, MEL, AFO, AEL, EUO and FER. In a further preferred aspect, the oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the oligomerization catalyst comprises an MTT zeolite.

The oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present invention is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark VERSAL. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable oligomerization catalyst is prepared by mixing proportionate volumes of zeolite and alumina to achieve the desired zeolite-to-alumina ratio. In an embodiment, the MTT content may be about 5 to 85, for example about 20 to 82 wt % MTT zeolite, and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 µm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

The oligomerization reactor 32 may be operated at a temperature from about 180° C. (356° F.) to about 260° C. (500° F.). The oligomerization reactor in the second reaction unit 30 may be run at a pressure from about 2.1 MPa (300 psig) to about 8.4 MPag (1200 psig), and more preferably from about 4.9 MPa (710 psig) to about 7.6 MPa (1100 psig) or from about 5.6 MPag (800 psig) to about 6.9 MPa (1000 psig).

When an oligomerization reaction in second reaction unit 30 is performed according to the above-noted process conditions, a C4 olefin conversion of greater than or equal to about 95% is achieved, or greater than or equal to 97%. The resulting third reacted product stream in line 36 comprises olefins and may comprise a plurality of olefin products that are distillate range hydrocarbons.

The oligomerization catalyst can be regenerated upon deactivation. Suitable regeneration conditions include subjecting the oligomerization catalyst, for example, in situ, to hot air at 500° C. for 3 hours. To facilitate regeneration without downtime, a swing bed arrangement may be employed with an alternative oligomerization reactor. A regeneration gas stream may be admitted to the oligomerization reactor within second reaction unit 30 requiring regeneration. The regeneration gas may comprise air with an increased or decreased concentration of oxygen. Activity and selectivity of the regenerated catalyst is comparable to fresh catalyst.

The third reacted product stream in line 36 may be fractionated in an optional fractionation unit 40 to provide a specific boiling point range product such as distillate or gasoline or jet fuel as the second hydrogenation feed stream in line 52 to the hydrogenation unit 50. A plurality of streams may be produced, some of which may be evacuated from the process or recycled within the process. In a preferred embodiment, the second hydrogenation feed stream in line 52 predominately comprises distillate. Alternately, the third reacted product stream in line 36 may be directly fed to the hydrogenation unit 50 as the second hydrogenation feed stream in line 52.

A first hydrogenation feed stream comprising the first electrolyzer product stream in line 26 is fed to the hydrogenation unit 50. In a preferred embodiment, the first electrolyzer product stream may be fed to the hydrogenation unit 50 without alteration of temperature or pressure of the stream. A second hydrogenation feed stream comprising olefins in line 52 is also fed to the hydrogenation unit 50. In an aspect, the second hydrogenation feed stream and the first electrolyzer product stream may be derived from the first feed stream in line 12. The hydrogenation unit 50 may be in downstream communication with the first reaction unit 10 and the electrolyzer unit 20.

The hydrogenation unit 50 performs hydrogenation of olefins to paraffins. Hydrogenation is typically performed using a conventional hydrogenation or hydrotreating catalyst, and can include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like.

In an exemplary embodiment, hydrogenation is performed in the hydrogenation reactor within hydrogenation unit 50 that includes a platinum-on-alumina catalyst, for example about 0.5 wt % to about 0.9 wt % platinum-on-alumina catalyst. The hydrogenation reactor converts the olefins into a paraffin product having the same carbon number distribution as the olefins, thereby forming distillate-range paraffins suitable for use as jet and diesel fuel. An excess of hydrogen may be employed to ensure complete saturation such as about 1.5 to about 2.5 of stochiometric hydrogen.

Hydrogenation reaction conditions may comprise a temperature of from about 100° C. to about 300° C. or from 150° C. to about 250° C. or from about 165° C. to about 200° C. Hydrogenation reaction conditions may also comprise a pressure of from about 400 psig to about 800 psig or from about 500 psig to about 700 psig, a weight hourly space velocity (WHSV) of from about 1 to about 5 or from about 1.8 to about 4.2 or from about 2 to about 3. Hydrogenation reaction conditions may further comprise a hydrogen to olefins molar ratio of from 1 to about 5 or from about 1.5 to about 4 or from about 2 to about 3.

The hydrogenation unit 50 produces a hydrogenation product stream comprising paraffins in line 56. A portion of this hydrogenation product stream may be separated and used as diluent stream in line 58 and fed to the second reaction unit 30 or recycled within the hydrogenation unit 50 to help control the exotherm. In an aspect, the olefin content in the second combined hydrogenation feed stream in line 55 may comprise from about 5% to about 50% or from about 6% to about 30% or from about 7% to about 20% on a weight basis.

Starting with ethanol, the disclosed process can efficiently produce green jet fuel and green diesel fuel that meets applicable fuel requirements. Carbon recovery in the process can exceed 95%. Hydrogen used to produce paraffins meeting the SPK standards is produced by electrolysis of water generated in a first reaction unit.

SPECIFIC EMBODIMENTS

While the following is described in conjunction with specific embodiments, it will be understood that this description is intended to illustrate and not limit the scope of the preceding description and the appended claims.

A first embodiment of the disclosure is an apparatus comprising a dehydration unit to provide a first reacted product stream comprising olefins in a first reacted product line and a second reacted product stream comprising water in a second reacted product line; a dimerization reactor in communication with the first reacted product line to provide a first dimerized stream in a dimerized line; an electrolyzer in communication with the second reacted product line to provide an electrolyzed product stream in an electrolyzed product line; an oligomerization reactor in communication with the dimerized line to provide a third reacted product stream comprising olefins in a third reacted product line; a hydrogenation unit in communication with the electrolyzed product line and the third reacted product line as a hydrogenation feed stream; and a hydrogenation product line in communication with the hydrogenation unit to provide a hydrogenation product stream comprising paraffins. An embodiment of the disclosure is one, any or all of prior embodiments in this paragraph up through the first embodiment in this paragraph further comprising a compressor in communication with the first reacted product line.

An embodiment of the disclosure is one, any or all of prior embodiments in this paragraph up through the first embodiment in this paragraph further comprising a compressor upstream of the hydrogenation unit in communication with the electrolyzer product line. An embodiment of the disclosure is one, any or all of prior embodiments in this paragraph up through the first embodiment in this paragraph wherein the dehydration unit is operating under dehydration reaction conditions at a temperature of from about 400° C. to about 550° C. and a pressure of from about 317 kPa (gauge) (45 psig) to about 2068 kPa (300 psig a temperature of from about 400° C. to about 550° C. and a pressure of from about 317 kPa (gauge) (45 psig) to about 2068 kPa (300 psig). An embodiment of the disclosure is one, any or all of prior embodiments in this paragraph up through the first embodiment in this paragraph wherein the oligomerization reactor operates under oligomerization reaction conditions at a temperature from about 100° C. to about 260° C. and a pressure from about 2.1 MPa to about 8.4 MPa.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:
1. A hydrogenation apparatus comprising:
  a dehydration unit to provide a first reacted product stream comprising olefins in a first reacted product line and a second reacted product stream comprising water in a second reacted product line;
  a dimerization reactor in communication with said first reacted product line to provide a first dimerized stream in a dimerized line;
  an electrolyzer in communication with said second reacted product line to provide an electrolyzed product stream in an electrolyzed product line;
  an oligomerization reactor in communication with said dimerized line to provide a third reacted product stream comprising olefins in a third reacted product line;
  a hydrogenation unit in communication with said electrolyzed product line and said third reacted product line as a hydrogenation feed stream; and
  a hydrogenation product line in communication with said hydrogenation unit to provide a hydrogenation product stream comprising paraffins.

2. The hydrogenation apparatus of claim 1 further comprising a compressor in communication with said first reacted product line.

3. The hydrogenation apparatus of claim 1 further comprising a compressor upstream of said hydrogenation unit in communication with said electrolyzer product line.

4. The hydrogenation apparatus of claim 1 wherein the dehydration unit is operating under dehydration reaction conditions at a temperature of from about 400° C. to about 550° C. and a pressure of from about 317 kPa (gauge) (45 psig) to about 2068 kPa (300 psig a temperature of from about 400° C. to about 550° C. and a pressure of from about 317 kPa (gauge) (45 psig) to about 2068 kPa (300 psig).

5. The hydrogenation apparatus of claim 1 wherein the oligomerization reactor operates under oligomerization reaction conditions at a temperature from about 100° C. to about 260° C. and a pressure from about 2.1 MPa to about 8.4 MPa.

6. The hydrogenation apparatus of claim 1 further comprising: a fractionation unit in communication with said third reacted product line and a hydrogenation feed line in communication with said fractionation unit to provide said hydrogenation feed stream comprising a specific boiling point range product such as distillate or gasoline or jet fuel.

7. The hydrogenation apparatus of claim 1 further comprising: a surge drum in communication with said second reacted product line and upstream of said electrolyzer.

8. The hydrogenation apparatus of claim 1 wherein said second reacted product line is in communication with a feed line.

9. The hydrogenation apparatus of claim 1 wherein said feed line is in communication with a recycle feed line comprising a recycle feed stream of unconverted ethanol which is in communication with said dehydration unit.

10. The hydrogenation apparatus of claim 1 further comprising a diluent line comprising a diluent stream in communication with said hydrogenation product line and wherein said hydrogenation feed line, said oligomerization reactor and said dimerization reactor are in communication with said diluent line.

* * * * *